United States Patent [19]

Iijima et al.

[11] Patent Number: 4,948,589
[45] Date of Patent: Aug. 14, 1990

[54] GRANULAR COMPOSITION FOR RUMINANT

[75] Inventors: Hitoshi Iijima; Masayuki Kiuchi; Masahiro Nakao; Kunio Nishimura, all of Kawasaki; Shigeaki Sato, Tokyo, all of Japan

[73] Assignee: Showa Denko Kabushiki Kaisha, Tokyo, Japan

[21] Appl. No.: 293,783

[22] Filed: Jan. 5, 1989

[51] Int. Cl.$^5$ .......................... A23K 1/18; A61K 9/16
[52] U.S. Cl. .................................... 424/438; 424/442; 424/490; 424/498
[58] Field of Search ................ 424/490, 438, 442, 498

[56] References Cited

U.S. PATENT DOCUMENTS

| T 100,404 | 3/1981 | Wu | 424/438 |
|---|---|---|---|
| 3,492,398 | 1/1970 | Marco et al. | 424/438 X |
| 3,697,640 | 10/1972 | Grant et al. | 424/438 |
| 4,675,175 | 6/1987 | Autant et al. | 424/495 |
| 4,713,245 | 12/1987 | Ando et al. | 424/438 |
| 4,842,863 | 6/1989 | Nishimura et al. | 424/438 |

FOREIGN PATENT DOCUMENTS 0936386 9/1963 United Kingdom ................ 424/438

Primary Examiner—Thurman K. Page
Attorney, Agent, or Firm—Sughrue, Mion, Zinn, Macpeak & Seas

[57] ABSTRACT

A granular composition for a ruminant containing as a main component choline or a physiologically acceptable derivative thereof, wherein the composition is prepared by (1) granulating the choline or it derivative having an average particle size of 100 $\mu$m or less and a maximum particle size of 150 $\mu$m or less, an excipient having an average particle size of 10 $\mu$m or less and a maximum particle size of 20 $\mu$m or less, and a hydrophobic binder under a relative humidity of 10% or less by using an agitation granulator, followed by cooling, separating and classifying the resultant granules to obtain spherical granules having a particle size of 0.5 to 2.5 mm and (ii) forming a thin film on the surface of the granules at a temperature of at least 5° C. less than a melting point of the binder and 5° C. to 25° C. less than a melting point of the overcoating agent under a relative humidity of 30% or less in an agitation granulator by adding 20 to 40 parts by weight, based on 100 parts by weight of the granules, of a heated molten mixture of a hydrophobic overcoating agent and a solubility modifier in the form of a fine powder in a weight ratio of 1:0.2–1.

7 Claims, No Drawings

4,948,589

GRANULAR COMPOSITION FOR RUMINANT

BACKGROUND OF THE INVENTION

1. Field of the Invention

The present invention relates to a granular composition for a ruminant containing choline or a physiologically acceptable derivative thereof having a high deliquescent property. More specifically, it relates to a granular composition for a ruminant in which choline or a physiologically acceptable derivative thereof usually fed with, for example, an animal feed, is protected from, for example, the action of microorganisms and a rumen solution present in a rumen of a ruminant and from the ruminating action and is digested and absorbed in an abomasum and downstream thereof.

2. Description of the Related Art

Choline and the physiologically acceptable derivatives thereof (i.e., sometimes referred to as "cholines" hereinbelow) are remarkably deliquescent, and, since they become liquid by absorbing humidity moisture when simply allowed to stand in atmospheric conditions, even the granulation thereof is quite difficult in the art. Accordingly, at present, liquid cholines and cholines adsorbed on powdered carriers (e.g., 50% choline adsorbed on cone cob meal) are produced, other than crystalline cholines. These cholines are used as a feed additive for monogastric animals, but are not used for ruminants such as cattles and sheep because they decompose in the rumen thereof, whereby they are not effectively utilized in an abomasum and an unpreferably large amount of the cholines is required.

As is known in the art, when physiologically active substances are directly orally fed to ruminants, most of those substances are decomposed by a variety of organisms present in the rumen thereof or a rumen solution and the physiological activities thereof are lost, and therefore, these physiologically active substances cannot be effectively utilized.

Thus, a so-called rumen-bypass granular agent, i.e., an agent which is not solubilized or decomposed in the rumen and is dissolved and absorbed in the abomasum and downstream thereof, is important to an effective utilization of physiologically active substances in ruminants, and various such granular agents have been developed.

For example, JP-B(Kokoku)-48-12785 (i.e., U.S. Pat. No. 3541204) proposes a controlled release granular composition for feeding to ruminants by coating the granular agent with a continuous film of one or more protective substances. Various protective substances are also discloses in JP-B-56-1057, JP-B-59-105780, and JP-A(Kokai)-58-175449.

Furthermore, JP-A-60-141242 proposes a granular agent obtained by covering physiologically active substances with a $C_{14}$–$C_{22}$ fatty acid, followed by a coating thereof with the above-mentioned protective substances.

The above-mentioned proposals can be practically applied to physiologically active substances having a relatively small solubility such as methionine and tryptophan and at most glucose. However, when these proposals are applied to cholines, the resultant granules are dissolved or decomposed in a ruminant because only cholines have the specifical solubility and deliquescent property, and furthermore, the granulation per se is difficult.

SUMMARY OF THE INVENTION

Accordingly, the objects of the present invention are to eliminate the above-mentioned disadvantages of the prior art and to provide a granular composition for a ruminant and containing choline capable of reaching an abomasum and the downstream thereof substantially in the form of granules, without easily dissolved or decomposed in the rumen.

Other objects and advantages of the present invention will be apparent from the following description.

In accordance with the present invention, there is provided a granular composition for a ruminant containing, as a main component, choline or a physiologically acceptable derivative thereof, wherein the composition is prepared by (i) granulating the choline or its derivative having an average particle size of 100 μm or less, preferably 50 μm or less and a maximum particle size of 150 μm or less, preferably 100 μm or less, an excipient having an average particle size of 10 82 m or less and a maximum particle size of 20 μm or less, and a hydrophobic binder under a relative humidity of 10% or less by using an agitation granulator equipped with a stirring means and a chopping means, followed by cooling, separating and classifying the resultant granules to obtain spherical granules having a particle size of 0.5 to 2.5 mm, preferably 0.7 to 2.3 mm and (ii) forming a thin film on the surface of the granules at a temperature of at least 5° C. less than a melting point of the binder, and 5 to 25° C. less than a melting point of the hydrophobic overcoating agent under a relative humidity of 30% or less in an agitation granulator at least equipped with a stirring means, by adding 20 to 40 parts by weight, based on 100 parts by weight of the granules, of a heated molten mixture of a hydrophobic overcoating agent and a solubility modifier in the form of a fine powder in a weight ratio of 1:0.2–1.

DESCRIPTION OF THE PREFERRED EMBODIMENTS

The choline derivatives usable in the present invention include, for example, choline chloride, choline phosphate, choline bitartrate, choline gluconate, choline dihydrogen citrate, choline fumarate, choline carbonate, and choline pyrophosphate. The preferable derivatives are choline chloride and choline phosphate.

Although there are no critical limitations to the amount of the cholines in the composition, the preferable amount is 40% to 70% by weight, more preferably 40% to 55% by weight in the granules before overcoating and 28% to 58% by weight, more preferably 30% to 50% by weight, in the total granular composition. The preferable upper limit mainly depends upon the agitation granulation and overcoating conditions for obtaining the desired granular composition and the preferable lower limit depends upon the practical and economical viewpoints.

The excipients usable in the present invention are those which are not or only slightly soluble under a neutral condition, but soluble in an acidic condition and acceptable to the living body. Such excipients include, for example, magnesium oxide or a mixture of magnesium oxide and at least one component selected from the group consisting of talc, calcium carbonate, magnesium carbonate, dibasic calcium phosphate ($CaHPO_4$), calcium phosphate [$Ca_3(PO_4)_2$], calcium oxide, calcium hydroxide, and calcium sulfate, at a weight ratio of less than 1:5, preferably 1:1–0.2.

The powder particle size of the excipients should be such that an average particle size is 10 μm or less, preferably 1 to 7 μm, and the maximum particle size is 20 μm or less, preferably 10 μm or less. The actually available excipients such as MgO, $MgCO_3$, $CaCO_3$ generally have a size of about 1 to 7 μm even in the secondary particles. When the particle size becomes smaller, the durability of the granular composition tends to be improved. In the case of, for example, talc, dibasic calcium phosphate and tribasic calcium phosphate, the above-specified particle size should be satisfied as a primary particle.

Although there are no critical limitations to the amount of the excipient in the composition, the preferable amount is 10% to 50% by weight, more preferably 25% to 40% by weight in the granules before overcoating and 7% to 42% by weight, more preferably 18% to 35% by weight in the total granular composition. The preferable upper limit depends upon the practical and economical viewpoints and the preferable lower limit depends upon the accomplishment of the desired effects or properties of the rumen-bypass agent.

The binders usable in the present invention should be hydrophobic and preferably have a melting point of 40° C. to 100° C., more preferably 45° C. to 90° C., and will not cause problems when fed as an animal feed additive to animals, and which do not adversely affect, or are not reactive with, the cholines in the granular compositions. It should be noted that when the melting point of the binder is less than the body temperature of a ruminant, e.g., 37° C.–41° C. in the case of cattles, the binder of the granules is melted and the mechanical strength becomes weak.

Typical examples of such binders are hydrogenated tallow, hydrogenated lard, hydrogenated palm oil, hydrogenated bean oil, hydrogenated coconut oil, hydrogenated fish oil, hydrogenated cottonseed oil, palmitic acid, and stearic acid, candelilla wax, carnauba wax, and bees wax, all having a melting point of 40° C. to 100° C.

Although there are no critical limitations to the amount of the binder in the composition, the preferable amount is 10% to 30% by weight, more preferably, 15% to 30% by weight in the granules. Basically, the durability of the granular composition increases with the increase in the amount of the binder within the limited range and it is recommendable to use a larger amount of the binder when the particle size of the cholines is small.

The hydrophobic overcoating agents usable in the present invention are the same as the above-mentioned hydrophobic binders, although different compounds in the production of the present granular compositions can be used. The overcoating agent is used for overcoating granules to hold a solubility modifier under the rumen conditions.

Although there are no critical limitations to the amount of the overcoating agent in the composition, the preferable amount is 50% to 80% by weight, more preferably, 50% to 75% by weight in the overcoating composition.

The solubility modifier usable in the present invention should be in the form of fine powder particles, e.g., 10 μm or less. Examples of such a solubility modifier are MgO, $CaHPO_4 \cdot 2H_2O$, CaO, $Ca_3(PO_4)_2$, $CaCO_3$, talc, and $Ca(OH)_2$. These solubility modifiers are stable under neutral conditions (i.e., pH=6–8) in the rumen, but are disintegrated or solubilized under acidic conditions (i.e., pH =3 or less) in the abomasum and downstream thereof, are optionally used during the granulation.

Although there are no critical limitations to the amount of the solubility modifiers in the composition, the preferable amount is 20% to 50% by weight, more preferably, 25% to 50% by weight in the overcoating composition.

The granular composition according to the present invention may optionally contain, in addition to the above-mentioned essential constituents, any ingredients conventionally used in the animal feed, especially for a ruminant, so long as the desired properties are not adversely affected, preferably in an amount of less than 10% by weight in the granular composition. Examples of such ingredients are $Fe_2O_3$, $Fe_2(CO_3)_3$, CoO, CuO, $MnCO_3$, $ZnCO_3$, and ZnO.

According to the present invention, the cholines having an average particle size of 100 μm or less, preferably 50 μm or less, more preferably 10 to 30 μm and a maximum particle size of 150 μm or less, preferably 100 μm or less, more preferably 50 μm or less are granulated, together with the above-mentioned excipient having an average particle size of 10 μm or less, preferably 1 to 7 μm and the above-mentioned hydrophobic binder under a relative humidity of 10% or less, preferably 4% or less, in the above-specified agitation granulator.

According to the present invention, the particle size of the cholines should be as specified above to obtain the desired granular composition. This is because not only the presence of the overcoat but also the presence of the hydrophobic binder in the inside structure of the particles are required in the present granular composition. The hydrophobic binder should be relatively uniformly compatible with the cholines and the excipient. When the average particle size of the cholines is large, the uniformity sufficient to obtain the desired properties is difficult to be attained. Furthermore, when the coarse particles are present, the system tends to become nonuniform and therefore, the maximum particle size of the cholines should be limited.

According to the present invention, the cholines are first ground in an appropriate grinder (e.g., a jet grinder, a ball mill, a high speed rotational grinder) to obtain the powder particles having the above-specified particle size. However, since the cholines are remarkably hydroscopic and deliquescent, the grinding operation and the subsequent granulation operation must be carried out under conditions such that the cholines are not easily deliquesced. The inventors have found that such operations can be effected only when the relative humidity is 10% or less. This can be carried out by grinding the cholines under a high temperature heating condition, preferably, while introducing dry air or under a sealed condition. Any conventional grinder such as a jet grinder, a ball mill, a high speed rotational grinder can be used as long as the above-mentioned operation conditions and the particle size limitations can be realized.

The granulation of the cholines is carried out together with the excipient and the hydrophobic binder under a relative humidity of 10% or less, preferably 4% or less, in the above-specified agitation granulator.

The binder content is preferably within the range from 10% to 30% by weight in the granules before overcoating, as mentioned above. Generally speaking, in the case of most starting materials, when the amount of the binder is lower than 10%, the granulation becomes difficult, whereas, when the amount of the binder is larger than 30%, the particle sizes become larger, i.e., coarse powder particles are sometimes formed, and the desired granulation becomes difficult, the binder ratio should be controlled, depending upon the kinds and the particles sizes of the cholines and the excipients, to the constant range, e.g., ±3%.

In a conventional granulation operation, aqueous binders are generally used. However, when a deliquescent substance such as choline is granulated, the deliquescent substance dissolves in the water of the aqueous binder and adheres to the wall surfaces of the granulators and, in an extreme case, becomes sherbet-like, which is impossible to be granulated.

The granulation is possible by using commercially available powder having an aqueous solution adsorbed thereto, but even if the granular composition is coated with a hydrophobic film to improve the durability thereof in the rumen, because of the absence of the compatibility with the aqueous cholin solution adsorbed, the coating exhibiting the desired bypass effect cannot be obtained. Thus, a granular agent granulated basically in a non-aqueous system is effective in the present invention.

For a non-aqueous granulation, a method using a molten binder (i.e., molten binder method) and a method using a binder dissolved in an organic solvent (i.e., organic solvent method) are considered to be applicable for the purpose of the present invention. However, the organic solvent method is not preferable because the resistance against a rumen solution is not sufficient because the organic solvent is removed, resulting in a high pore ratio. Accordingly, the molten binder method is most suitable for the present invention.

As mentioned above, since cholines are highly deliquescent, the granulation must be carried out under an atmosphere at a relative humidity of 10% or less. When the granulation is carried out in an open air system, the cholines absorb moisture in the air and dissolve therein. Thus, the same results occur as in the above-mentioned aqueous granulation. Accordingly, the above-mentioned grinding conditions must be maintained in the granulation step.

As granulation methods, although spray granulation, tumbling granulation, fluidized granulation, extrusion granulation, compression granulation, agitation granulation and the like are known in the art. However, for the purpose of the present invention, the agitation granulation should be used because the void volume within the granules can be minimized and the thin film coating formed on the surface of the granule to provide the desired resistance to solubilization or decomposition by the rumen solution.

We have found that, when the agitation granulation is used, relatively spherical or round granulated particles, which are suitable for the subsequent coating, can be advantageously obtained and the binder content may be optimized within the narrow range. In the case of the agitation granulation, the tumbling granulation is simultaneously effected and, therefore, the fluidizable binder is migrated to the surface of the granules during the granulation to form a surface layer. As a result, the cholines and other powder to be protected is relatively located in the inside portion of the granules. For this purpose, the granulation must be carried out at a temperature of more than the melting point of the binder. Thus, a part of the properties necessary for the rumen-bypass agents can be obtained only by the agitation granulation. During the subsequent coating, not only the simple tumbling but also the pressurized compacting can be effected and, therefore, the dense overcoating can be formed. The particle agglomeration can be obviated by the presence of the main axis (e.g., stirrer having rotating blade).

The agitation granulator to be used in the present invention should be equipped with a stirring means such as a stirrer with, for example, relatively large-sized rotating blades for stirring the particles to the granulated and with a chopping means such as a chopper with, for example, relatively small-sized rotating blades for agglomerating the compounds and chopping the agglomerated or largely granulated particles. For example, in the case of the granulator having a capacity of 10 liters, the preferable revolution number of the stirring means is several hundreds r.p.m. and that of the chopping means is several thousands r.p.m. Thus, the particles are desirably granulated in the uniform shape and size.

Furthermore, the granulators preferably usable in the present invention are those having a structure capable of being heated from the outside (e.g., a heater) and capable of controlling the humidity inside of the granulator where powder particles are exposed (e.g., a dehumidifier), because the molten granulation is used in the present invention. The present inventors have used a vertical type agitation granulator model VG-10L available from Fuji Sangyo K.K., Japan or Nara jacket type-LMA-10 or type-HMA-65 available from Nara Kikai K.K., Japan. The granulator is operated by using the above-mentioned binder at a granulating temperature higher than the melting point of the binder under the conditions of, for example, a revolution number of a main stirrer of 200 rpm to 300 rpm in the type-LMA-10 or 80 to 200 rpm in the type-HMA-65 and a revolution number of a chopper of 1500 rpm to 3000 rpm, although these revolution numbers largely depend upon the size of the granulator, the types of the rotating blades. The choline granules thus obtained are coated with the hydrophobic overcoating agent and exhibit a primary resistance to solubilization in the rumen solution although it is not still sufficient for the purposes of the present invention.

The particle size distribution of the granule after agitation granulation is relatively large, and therefore, the resultant granules should be sifted, based upon the size of the granules, to obtain granules suitable for use as a feed additive for ruminants. The preferable size of the particle is 0.5 to 2.5 mm, more preferably 0.7 to 2.3 mm, as a diameter. When the particle size of the final product is too large, the granules are sometimes crushed during the ruminating action. Contrary to this, when the particle size is too small, the overcoating sometimes become incomplete and, therefore, the desired durability cannot be obtained. The reasons for the incomplete coating are that, since the small-sized fine particles are likely to be agglomerated even in the agitation coating so that the agglomerated particles become irregular. Thus, the resultant particles become to be difficult for overcoating. When the granules are shifted, the granules should be cooled to less than a melting point of the binder, for example, 40° C. or less, preferably room temperature, to solidify the binder. Otherwise, defects are generated in the surface layer of the granules and the desired resistance to solubilization by the rumen is lost.

According to the present invention, the granules of the cholines obtained above are overcoated with a thin film by adding 20 to 40 parts, preferably 20 to 30 parts by weight, of a molten mixture, upon heating, based upon 100 parts by weight of the granules, of a hydrophobic overcoating agent and a solubility modifier in the form of a powder at a weight ratio of 1:0.2–1, preferably 1:0.25–1.

The overcoating is also effected, as in the case of the above-mentioned grinding and granulating, by using, for example, non-aqueous overcoating agent under conditions such that the absorption of the granules does not occur.

However, the overcoating temperature is lower, by at least 5° C., more preferably by 10° C. to 15° C., than a melting point of the binder included in the granules, and by 5° C. to 25° C., preferably by 5° C. to 15° C., than a melting point of the overcoating agent, unlike the granulating temperature and the overcoating agent is introduced in a molten condition.

The present invention is characterized by adding the molten overcoating agent (e.g., wax) onto the surface of the granulated particle surfaces and, while solidifying on the surface, the desired overcoat is formed. Accordingly, the temperature of the granules to be coated should be lower, by at least 5° C., than the melting point of the binder. If not, the binder is softened and melted and, as a result, the agglomeration and granulation during the overcoating unpreferably occur.

On the other hand, the temperature of the granules to be coated should be lower, 5° C. to 25° C., than the melting point of the overcoating agent. When the temperature of the granules is the melting point or more of the overcoating agent, the solubility modifier powder must be added in a weight ratio of 1:1 or more, based on the overcoating agent. Otherwise, the overcoating layer cannot be solidified and, as a result, the agglomeration of the granules occur. When the granules are cooled to solidify during this operation, cracks are unpreferably generated in the overcoatig layer. Contrary to this, when the temperature of the granules to be overcoated is too low, the powdered overcoating agent is rapidly cooled on the surfaces of the granules for a relatively short time, the necessary stretchability cannot be afforded to the overcoat layer. Thus, the desired overcoat layer cannot be obtained. The above-mentioned conditions are essential for forming the desired overcoating layer.

The binder and the overcoating agent may be the same or different, but the use of the same or similar substances is preferable because the good coating can be obtained when the compatibility of the binder with the overcoating agent is good.

The overcoating of the present invention can be effected in an agitation type coating apparatus, as long as the coating apparatus can be heat controlled so that the overcoating can be effected at a temperature of lower, by at least 5° C., than the melting point of the binder. The overcoating temperature depends upon a combination of the binder and the overcoating agent. The overcoating temperature is lower, by 5° C. or more, than a melting point of the binder and, by 5° C. to 15° C., than a melting point of the overcoating agent. Thus, since the temperature must be controlled within about 10° C., the kind of the overcoating agent is limited. The present inventors prefer to use the above-specific agitation granulator type coating apparatus, without using the chopping means. When the above-mentioned conditions are fulfilled, the desired functions of the rumen-bypass granular compositions can be effected.

As mentioned above, as the overcoating substance, a mixture of the molten hydrophobic overcoating agent and the finely powdered solubility modifier in a weight ratio of 1:0.2–1.0, preferably 1:0.25–1.0 is used in an amount of 20 to 40 parts by weight, preferably 20 to 30 parts by weight, based on 100 parts by weight of the granular composition. When the amount of the mixture of the molten overcoating agent and the finely powdered solubilizing modifier is too small, it is difficult to obtain the preferable overcoating film sufficient to bypass the rumen. Contrary to this, when the amount is too large, the choline content in the granules becomes undesirably small. When the ratio of the overcoating agent to the solubility modifier is too large, the solubility in the abomasum becomes undesirable. Contrary to this, when the ratio is too small, defective overcoating film is formed and the durability in the rumen is spoiled.

The resultant granules are cooled to room temperature. Although there are no critical limitations to the particle size of the final granular composition, the size is preferably 0.5 to 2.5 $\mu$m, more preferably 0.7 to 2.3 $\mu$m.

EXAMPLES

The present invention will now be further illustrated by, but is by no means limited to the following Examples.

EXAMPLES 1

(1) Granulation

Choline chloride was ground under an air at a relative humidity of 4% in a jet grinder to obtain the powder particles having an average size of 20 $\mu$m. A 1400 g amount of the resultant choline chloride powder, together with 740 g of magnesium oxide, 430 g of talc, and 350 g of hydrogenated tallow (m.p. =60° C.), were granulated upon heating at 70° C. for 40 minutes by introducing a dry air having a relative humidity of 1% in a LMA-10 type agitation granulator (available from Nara Kikai K.K., Japan) under the conditions of a revolution number of a main axis of 250 rpm and a revolution number of a chopper of 3000 rpm.

The resultant granules obtained above were cooled to room temperature by a fluidized cooler, followed by classifying in an Allgaier screen classifier to obtain the granules having a size of #8 to 32 mesh (Tyler). A 2000 g amount of the granules thus obtained was heated at 50° C. in an agitating coater and 400 g of hydrogenated tallow (m.p. =60° C.) in a molten state upon heating to 80° C. and 115 g of magnesium oxide were added thereto to overcoat the granules. After cooling, the desired granular composition of choline chloride was obtained.

(2) Dissolution Test

A 1 g amount sample of the resultant feed additive granules was immersed in 50 ml of a buffer solution having a pH 6.2, which correspond to a rumen solution, followed by shaking at 39° C. for 18 hours. Thereafter, the sample granules were shaken at 39° C. for 4 hours in 50 ml of a buffer solution having a pH of 2.0 corresponding to an abomasum solution.

The amount of choline chloride dissolved into the buffer solutions corresponding to the rumen and abomasum solutions were quantitatively determined. The results are shown as a dissolution rate (%)

| | |
|---|---|
| Dissolution rate in rumen corresponding solution | 19% |
| Dissolution rate in abomasum corresponding solution | 90% |

EXAMPLE 2

(1) Granulation 1400 g amount of choline phosphate having an average particle size of 20 μm, 800 g of magnesium oxide, 400 g of talc, and 320 g of hardened tallow (m.p. =58° C.) were granulated in a VG-10 agitating granulator under the following conditions.

| | |
|---|---|
| Granulating temperature | 80° C. |
| Environmental humidity | 4% |
| Revolution number of main axis | 200 rpm |
| Revolution number of chopper | 3000 rpm |

The resultant granules were cooled to room temperature and the granules having a size of 8-32 mesh were screen classified. A 2000 g of the resultant granules was coated with 380 g of hardened tallow (m.p.=58° C.) in the molten state heated to 80° C., upon heating at 48° C., and 120 g of tribasic calcium phosphate in a Lodige type agitation coater.

(2) Dissolution Test

The resultant granules were evaluated with regard to the dissolution rate in the same manner as in Example 1.

| | |
|---|---|
| Dissolution rate in rumen corresponding solution | 15% |
| Dissolution rate in a abomasum corresponding solution | 94% |

As is clear from the above-mentioned results, the desired granular composition can be obtained.

COMPARATIVE EXAMPLES

1. When the dissolution test of Example 1 was carried out with respect to the inner granules of Example 1 in which the overcoating was not applied, the dissolution rate in the rumen solution was 99%. As a result, the choline chloride was substantially completely dissolved in a rumen corresponding solution. Thus, when the coating is not applied, the desired resistance is not obtained.

2. When the inner granules of Example 1 was overcoated with a coating agent containing a lower content of the solubility modifier (i.e., 60 g of magnesium carbonate in the formulation of Example 1), the results are as follows.

| | |
|---|---|
| Dissolution rate in a rumen corresponding solution | 9% |
| Dissolution rate in an abomasum corresponding solution | 63% |

Thus, substantial efficiency was as low as 52%

3. A 540 g of choline chloride, 290 g of calcium carbonate, and 170 g of talc were granulated with alcohol (i.e., 400 g of a 1:3 mixture of H$_2$O/ethanol) to prepare the granules having no sufficient resistance as the inner granules. The resultant granules were coated with the coating agent similar to that used in Example 1, under the same conditions as in Example 1.

As a result of the dissolution test used in Example 1, the dissolution rate in a rumen corresponding solution was 56%. Thus, the granules having sufficient resistance were not obtained.

4. From 1400 g of powdered choline having an average particle size of 195 μm, 740 g of magnesium carbonate, 430 g of talc, and 280 g of tallow, the similar granules were prepared, followed by overcoating in the manner as in Example 1.

As a result, the dissolution rate of the granules in a rumen was 37%. Thus, the resultant sample has a relatively high solubility.

We claim:

1. A granular composition for a ruminant comprising as a main component choline or its derivative selected from the group consisting of choline chloride, choline phosphate, choline bitartrate, choline gluconate, choline dihydrogen citrate, choline fumarate, choline carbonate, and choline pyrophosphate, said composition being prepared by
   (i) granulating the choline or its derivative having an average particle size of 100 μm or less and a maximum particle size of 150 μm or less, an excipient having an average particle size of 10 μm or less and a maximum particle size of 20 μm or less, and a hydrophobic binder under a relative humidity of 10% or less by using an agitation granulator equipped with a stirring means and a chopping means, followed by cooling, separating and classifying the resultant granules to obtain spherical granules having a particle size of 0.5 to 2.5 mm, and
   (ii) forming a thin film on the surface of the granules at a temperature of at least 5° C. less than the melting point of the binder and 5° C. to 25° C. less than the melting point of the overcoating agent under a relative humidity of 30% or less in an agitation granulator by adding 20 to 40 parts by weight, based on 100 parts by weight of the granules, of a heated molten mixture of a hydrophobic overcoating agent and a solubility modifier in the form of a fine powder in a weight ratio of 1:0.2-1.

2. A granular composition as claimed in claim 1, wherein the composition comprises 28% to 58% by weight of the choline or its derivative, 7% to 25% by weight of the binder, 7% to 42% by weight of the excipient, 8% to 24% of the hydrophobic overcoating agent, and 3% to 15% of the solubility modifier.

3. A granular composition as claimed in claim 1, wherein said choline derivative is choline chloride or choline phosphate.

4. A granular composition as claimed in claim 1, wherein said excipient is magnesium oxide or a mixture of magnesium oxide and at least one component selected from the group consisting of talc, calcium carbonate, magnesium carbonate, dibasic calcium phosphate (CaHPO$_4$), and calcium phosphate [Ca$_3$(PO$_4$)$_2$].

5. A granular composition as claimed in claim 1, wherein said hydrophobic binder is at least one member selected from the group consisting of hydrogenated tallow, hydrogenated lard, hydrogenated palm oil, hydrogenated bean oil, hydrogenated coconut oil, hydrogenated fish oil, hydrogenated cottonseed oil, palmitic acid, stearic acid, candelilla wax, carnauba wax, and bees wax, all having a melting point of 40° C. to 100° C.

6. A granular composition as claimed in claim 1, wherein said hydrophobic overcoating agent is at least one member selected from the group consisting of hydrogenated tallow, hydrogenated lard, hydrogenated palm oil, hydrogenated bean oil, hydrogenated coconut oil, hydrogenated fish oil, hydrogenated cottonseed oil, palmitic acid, stearic acid, candelilla wax, carnauba wax, and bees wax, all having a melting point of 40° C. to 100° C.

7. A granular composition as claimed in claim 1, wherein said solubility modifier is at least one member selected from the group consisting of magnesium oxide, $CaHPO_4.2H_2O$, $CaO$, $Ca_3(PO_4)_2$, $CaCO_3$, talc, and $Ca(OH)_2$.

* * * * *